United States Patent
Bennett

(10) Patent No.: US 6,491,714 B1
(45) Date of Patent: Dec. 10, 2002

(54) SURGICAL TISSUE REPAIR AND ATTACHMENT APPARATUS AND METHOD

(76) Inventor: William F. Bennett, 5741 Bee Ridge Rd., Suite 470, Sarasota, FL (US) 34233

( * ) Notice: Subject to any disclaimer, the term of this patent is extended or adjusted under 35 U.S.C. 154(b) by 0 days.

(21) Appl. No.: 09/569,203

(22) Filed: May 11, 2000

Related U.S. Application Data

(60) Continuation-in-part of application No. 09/360,794, filed on Jul. 26, 1999, now Pat. No. 6,206,886, which is a division of application No. 08/850,526, filed on May 2, 1997, now Pat. No. 6,013,083.
(60) Provisional application No. 60/016,847, filed on May 3, 1996.

(51) Int. Cl.[7] ............................................... A61B 17/04
(52) U.S. Cl. ...................................................... 606/232
(58) Field of Search ................................ 606/213, 232, 606/74; 623/13.14, 14.12

(56) References Cited

U.S. PATENT DOCUMENTS

| | | | | |
|---|---|---|---|---|
| 3,695,271 A | * | 10/1972 | Chodorow ................... 606/233 |
| 4,287,807 A | * | 9/1981 | Pacharis et al. .............. 411/42 |
| 4,532,926 A | * | 8/1985 | O'Holla ....................... 606/220 |
| 4,534,350 A | * | 8/1985 | Golden et al. ............... 606/220 |
| 4,667,675 A | * | 5/1987 | Davis .......................... 24/71.1 |
| 4,669,473 A | * | 6/1987 | Richards et al. ............. 606/215 |
| 4,796,612 A | * | 1/1989 | Reese .......................... 606/72 |
| 4,950,285 A | * | 8/1990 | Wilk .......................... 24/16 PB |
| 5,053,047 A | * | 10/1991 | Yoon .......................... 606/223 |
| 5,269,809 A | * | 12/1993 | Hayhurst et al. ............ 606/151 |
| 5,324,308 A | * | 6/1994 | Pierce ......................... 606/232 |
| 5,350,399 A | * | 9/1994 | Erlebacher et al. ......... 128/899 |
| 5,370,661 A | * | 12/1994 | Branch ........................ 24/16 R |
| 5,462,542 A | * | 10/1995 | Alesi, Jr. ..................... 24/16 R |
| 5,500,000 A | * | 3/1996 | Feagin et al. ................ 606/213 |
| 5,584,835 A | * | 12/1996 | Greenfield ................... 606/232 |
| 5,613,283 A | * | 3/1997 | Yusfan ....................... 24/116 A |
| 5,713,903 A | * | 2/1998 | Sander et al. ................. 606/60 |
| 5,720,753 A | * | 2/1998 | Sander et al. ............... 606/104 |
| 5,810,854 A | * | 9/1998 | Beach ....................... 24/16 PB |
| 5,814,071 A | * | 9/1998 | McDevitt et al. ........... 606/144 |
| 5,906,631 A | * | 5/1999 | Imran ......................... 606/213 |
| 6,015,410 A | * | 1/2000 | Tormala et al. ............... 606/73 |
| 6,241,748 B1 | * | 6/2001 | Adams ........................ 606/220 |
| 6,241,749 B1 | * | 6/2001 | Rayhanabad ................ 606/232 |
| 6,348,053 B1 | * | 2/2002 | Cachia ......................... 606/68 |

* cited by examiner

Primary Examiner—David O. Reip
Assistant Examiner—Daniel Jacob Davis
(74) Attorney, Agent, or Firm—Charles J. Prescott

(57) ABSTRACT

A surgical apparatus for anchoring and reattachment of torn tissue such as a rotator cuff against on the outer or exterior surface of a tissue substrate. The invention includes a tissue substrate anchor such as that having expandable wings, an elongated suture member securable at its proximal end to the tissue substrate anchor, and a torn tissue retainer lockingly attachable along the length of the suture member by mating interlocking structure therebetween. Tension is applied to the free distal end of the suture member while the tissue retainer is non-reversibly moved longitudinally along on the suture member to secure the torn tissue against the tissue substrate outer surface. A separate torn tissue gripping member may also be provided for broadened and enhanced torn tissue securement against the tissue substrate. In another embodiment, the tissue anchor is formed as a unit with the suture member enabling additional forms of tissue repair such as the closure of an internal meniscus tear or separation.

1 Claim, 14 Drawing Sheets

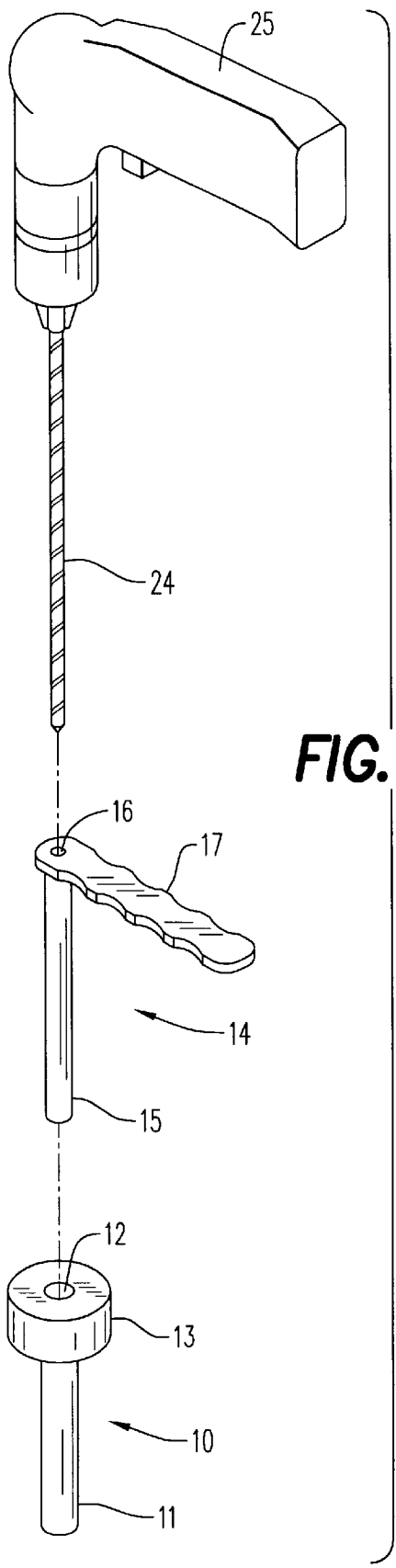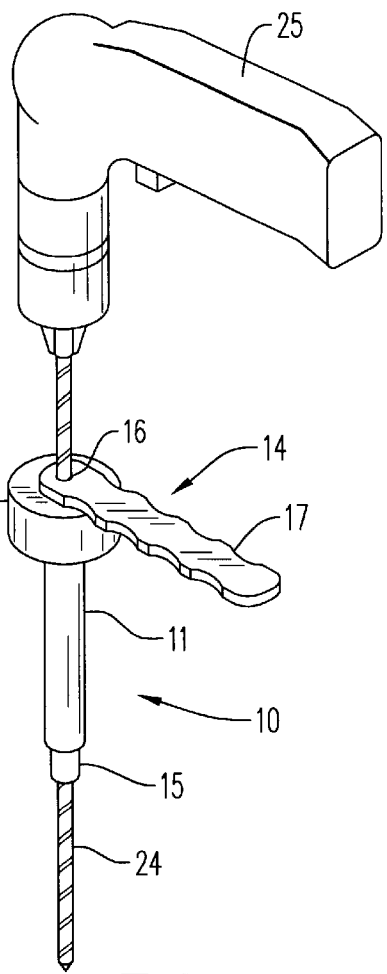
FIG. 1A
FIG. 1B

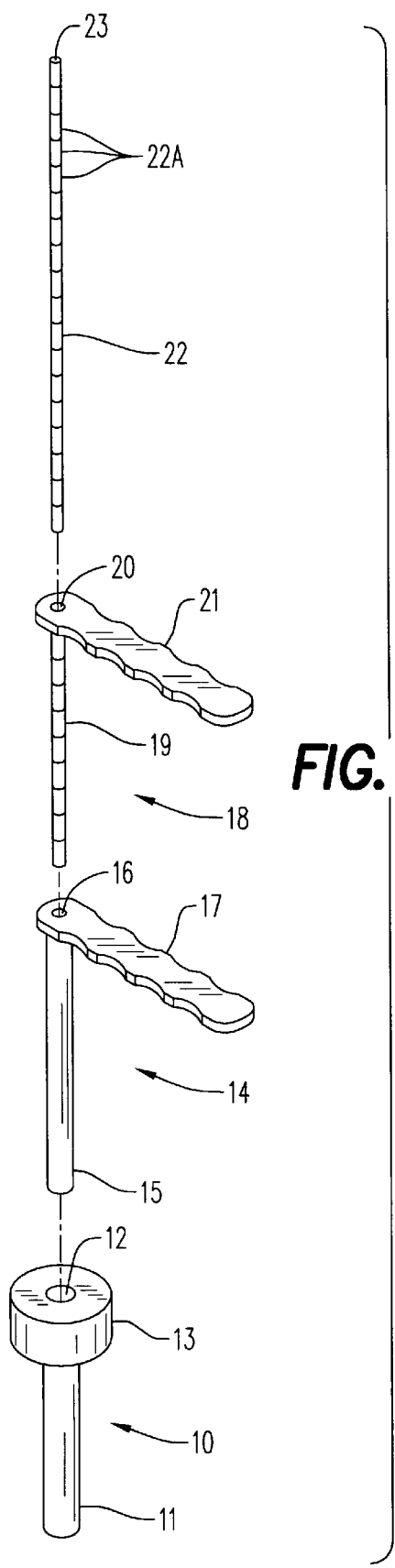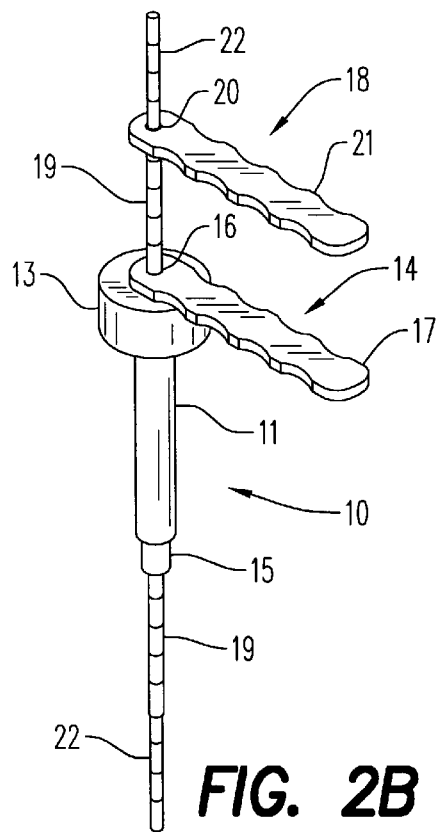
FIG. 2A
FIG. 2B

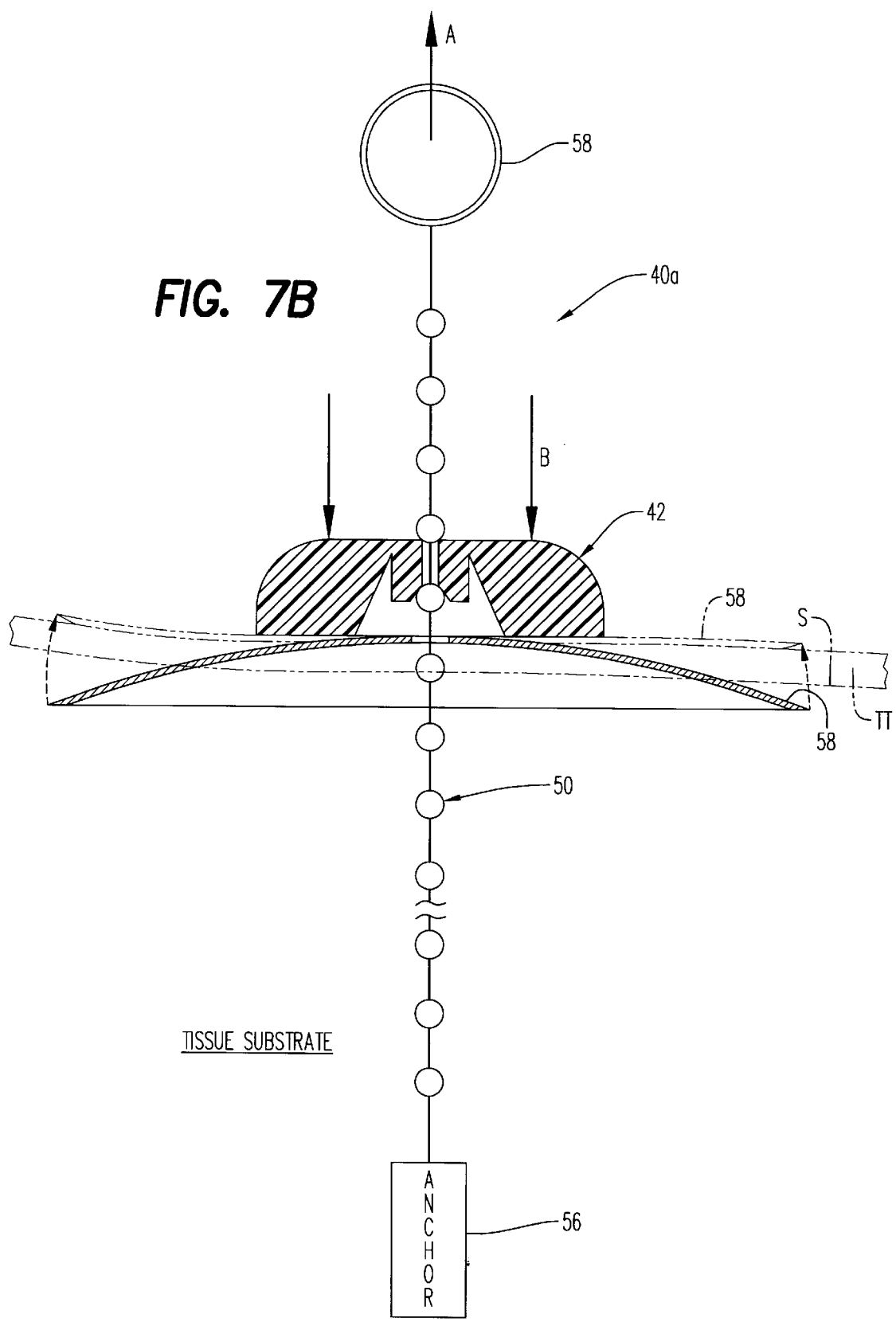

TISSUE SUBSTRATE

SURGICAL TISSUE REPAIR AND ATTACHMENT APPARATUS AND METHOD

This is a continuation-in-part of co-pending application Ser. No. 09/360,794, filed Jul. 26, 1999, now U.S. Pat. No. 6,206,886, which is a divisional of application Ser. No. 08/850,526, filed May 2, 1997, now U.S. Pat. No. 6,013,083 which claims benefit of No. 60/016,847 filed May 3, 1996.

BACKGROUND OF THE INVENTION

1. Scope of Invention

This invention relates generally to surgical apparatus and methods for repair of torn tissue, and more particularly to an apparatus and method for arthroscopic and general surgical repair of torn tissue and tissue reattachment by anchoring the tissue against the outer surface of tissue substrate.

2. Prior Art

The rotator cuff is composed of four tendons that blend together to help stabilize and move the shoulder. When a tear occurs in the rotator cuff of the shoulder, it is often necessary to reattach the torn tendon or tendons to the bone of the humeral head.

In a common prior art rotator cuff reattachment technique, the torn cuff is punctured by a punch, and prethreaded suture anchor screws (soft tissue fasteners) are drilled into the head of the humerus bone and the sutures threaded through the anchor screws are passed through the cuff in a difficult procedure using suture relay devices to pass the sutures through the tissue. After the suture strands are passed through the tissue, they are knotted and tied together to secure the reattached rotator cuff to the humerus head. Other types of prior art suture anchors are conically shaped members that are pressed into holes drilled into the bone and engage the cancellous mass surrounding the drilled hole.

A major problem with the above described suture anchoring technique is that the threaded suture anchor screws or conically shaped anchors are threadedly or otherwise secured to the cancellous bone mass beneath the near cortex of the head of the humerus, and depend on this cancellous mass for fixation. It is well known that the cancellous bone mass is susceptible to osteopenic changes (diminished amount of bone tissue).

As a result, the pull-out strength of suture anchors which are depend on the cancellous bone mass beneath the cortex of the bone is subject to becoming diminished with time, and the anchors will tend to loosen, thereby possibly requiring a second operation to remove the loosened suture anchor.

Another problem with the conventional technique is that, in most cases, the sutures are not passed through the tissue when the anchor is set, and thus a difficult procedural step is required using devices such as punches and suture relays to pass and tie the sutures through the torn tissue.

The present invention is distinguished over the prior art in general, by an apparatus and method for arthroscopic repair of torn tissue such as a rotator cuff wherein torn tissue such as a rotator cuff is positioned on the bone exterior by a tissue grasper. A cannula is inserted through the skin substantially to the torn tissue. A drill guide is inserted into the cannula, a drill bit is inserted into the drill guide, and a hole is drilled through the torn tissue and completely through the bone. The drill bit is removed and an inner cannula is passed through the drill guide until its distal end is engaged on the torn tissue or alternatively passed through the hole until its distal end is at the far end of the drilled hole. A soft tissue anchor having expandable wings at its distal end and sutures secured to an eyelet at its proximal end is releasably connected to the distal end of a tubular deployment tool with the free ends of the sutures extending through the deployment tool.

The deployment tool is passed through the inner cannula and drilled hole until the expandable wings clear the far end of the hole a sufficient distance to allow the wings to expand to a diameter larger than the diameter of the drilled hole. The deployment tool, inner cannula, drill guide, and cannula are removed and tension is applied to the suture to engage the expanded wings of the anchor on the exterior surface of the bone surrounding the drilled hole. A button is run down on the sutures through the cannula and secured on the torn tissue by the sutures such that the torn tissue is secured to the bone and the sutures are anchored to the hard exterior surface of the bone by the expanded anchor.

Unlike conventional soft tissues anchors which are anchored in the cancellous bone mass beneath the near cortex of the bone, the present invention in one embodiment provides a suture anchor which is engaged on the exterior of the far cortex of the bone and completely bypasses the cancellous bone mass. The cortex of the bone is much less susceptible to osteopenia than the cancellous interior of the bone.

With the present invention, the sutures are passed through the tissue when the anchor is set, and thus the difficult procedural step and use of devices such as punches and suture relays to pass and tie the sutures through the torn tissue is eliminated.

Calibrated markings on the deployment system of the present invention allow for precise measurement of the far cortex and precise measurement of the depth of insertion and engagement of the anchor device on the far cortex, such that structures beyond the cortex are not violated, and the button hold-down feature eliminates the traditionally difficult arthroscopic tying techniques.

In another broader aspect of the invention, the surgical apparatus includes any form of a tissue substrate anchor of a conventional well-known structure, an elongated suture member securable at its proximal end to the anchor, and a separate torn tissue retainer which lockably engages as desired along the length of the suture member. The suture member extending through the torn tissue from the anchor and the tissue substrate. The torn tissue retainer is movable along the length of the exposed portion of the suture member until it is tightly positioned against the torn tissue and automatically locked in that position by non-reversible lockable engagement with the suture member. A separate tissue gripping member formed preferably as a semi-flexible plate or disc having a substantially larger surface area than the tissue retainer is also provided for enhanced retention of the torn tissue in place against the outer surface of the tissue substrate.

Still another broad aspect of this invention is directed to a surgical apparatus which includes an integrally formed tissue substrate anchor having an elongated suture member formed as a unit therewith. A separate disc-shaped retainer lockingly engages with the exposed distal end of the suture portion at any desired point along the suture interlocking portion. The tissue retainer is therefore moveable along the length of the exposed engaging members of the suture member for tightening the tissue layer against the tissue substrate. Utilized another way, a tear such as that found within a torn meniscus may be reconnected utilizing this embodiment of the invention.

BRIEF SUMMARY OF THE INVENTION

This invention is directed to a surgical apparatus for anchoring and reattachment of torn tissue such as a rotator cuff against on the outer or exterior surface of a tissue substrate such as bone or cartilage. The invention includes a tissue substrate anchor such as that having expandable wings, an elongated suture member securable at its proximal end to the tissue substrate anchor, and a torn tissue retainer lockingly attachable along the length of the suture member by mating interlocking structure therebetween. Tension is applied to the free distal end of the suture member while the tissue retainer is moved longitudinally along the suture member, forcing the tissue retainer to secure the torn tissue against the tissue substrate outer surface. A separate torn tissue gripping member may also be provided for broadened and enhanced torn tissue securement against the tissue substrate.

It is therefore an object of the present invention to provide an apparatus and method for arthroscopic repair of torn tissue such as a rotator cuff which engages a suture anchor on the exterior of the far cortex of the bone and completely bypasses the cancellous bone mass.

It is therefore an object of the present invention to provide an apparatus and method for arthroscopic repair of torn tissue such as a, rotator cuff which passes the sutures through the tissue when the anchor is set, and eliminates the difficult procedural step and use of devices such as punches and suture relays to pass and tie the sutures through the torn tissue.

Another object of this invention is to provide an apparatus and method for arthroscopic repair of torn tissue such as a rotator cuff which utilizes suture anchoring apparatus having calibrated markings for precise measurement of the far cortex and the depth of insertion and engagement of the anchor device on the far cortex, such that structures beyond the cortex are not violated.

A further object of this invention is to provide an apparatus and method for arthroscopic repair of torn tissue such as a rotator cuff that utilizes a button hold-down feature which substantially eliminates traditionally difficult arthroscopic suture tying techniques.

A still further object of this invention is to provide an apparatus for arthroscopic repair of torn tissue such as a rotator cuff which is simple in construction, inexpensive to manufacture, and rugged and reliable in operation.

A yet further object of this invention is to provide a surgical apparatus for reattaching torn tissue in any form atop a tissue substrate of any consistency utilizing a conventional tissue substrate anchor and a unique elongated suture member which is lockingly interengageable to a tissue retaining member which lockably engage one to another after the proximal end of the suture member is attached to the anchor.

In accordance with these and other objects which will become apparent hereinafter, the instant invention will now be described with reference to the accompanying drawings.

The above noted objects and other objects of the invention are accomplished by the present invention in one embodiment wherein torn tissue such as a rotator cuff is positioned on the bone exterior by a tissue grasper. A cannula is inserted through the skin substantially to the torn tissue. A drill guide is inserted into the cannula, a drill bit is inserted into the drill guide, and a hole is drilled through the torn tissue and completely through the bone. The drill bit is removed and an inner cannula is passed through the drill guide until its distal end is engaged on the torn tissue or alternatively passed through the hole until its distal end is at the far end of the drilled hole.

A soft tissue anchor in one embodiment having expandable wings at its distal end and sutures secured to an eyelet at its proximal end is releasably connected to the distal end of a tubular deployment tool with the free ends of the sutures extending through the deployment tool. The deployment tool is passed through the inner cannula and drilled hole until the expandable wings clear the far end of the hole a sufficient distance to allow the wings to expand to a diameter larger than the diameter of the drilled hole.

The deployment tool, inner cannula, drill guide, and cannula are removed and tension is applied to the suture to engage the expanded wings of the anchor on the exterior surface of the bone surrounding the drilled hole. A button is run down on the sutures through the cannula and secured on the torn tissue by the sutures such that the torn tissue is secured to the bone and the sutures are anchored to the hard exterior surface of the bone by the expanded anchor.

A broader embodiment of the invention provides for the reattachment of any torn or damaged tissue or artificial tissue to any form of tissue substrate by the use of a tissue substrate anchor of any generally well known structure. A primary aspect of the broader invention is the utilization of an elongated suture member attachable at its proximal end to the anchor as or after it is positioned and secured within the tissue substrate. The distal exposed end portion of the suture member extends from the tissue substrate and through the torn or damaged tissue after being normally positioned atop the tissue substrate. Thereafter, a separate tissue retainer is lockably engaged along the exposed length of the suture member and tightened against the torn tissue to retain it in position against the tissue substrate. A separate tissue gripping plate positioned between the torn tissue and the corresponding surface of the tissue retainer may preferably be provided for enhanced torn tissue placement and retention.

BRIEF DESCRIPTION OF THE DRAWINGS

FIG. 1A is an exploded perspective view of the cannula and drill guide components of the apparatus in accordance with the present invention.

FIG. 1B is a perspective view of the cannula and drill guide components shown in an assembled condition.

FIG. 2A is an exploded perspective view of the cannula, drill guide, inner cannula, and anchor deployment tool components of the apparatus.

FIG. 2B is a perspective view of the cannula, drill guide, inner cannula, and anchor deployment tool components shown in an assembled condition.

FIG. 7B is a side elevation partial section view similar to FIG. 7A showing the addition of a separate tissue gripping member.

DETAILED DESCRIPTION OF THE INVENTION

Figure 3:
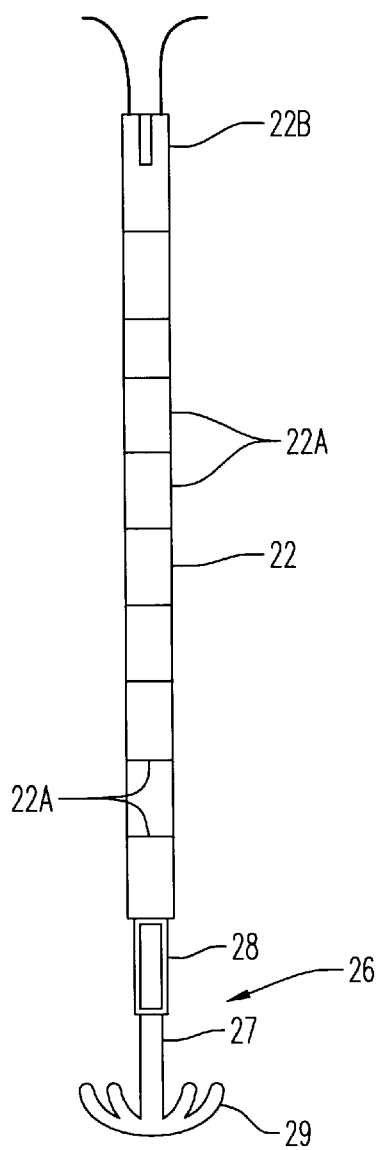
FIG. 3 is a side elevation of the suture anchor and anchor deployment tool in a releasably connected position.

Referring now to FIGS. 1A, 1B, 2A, and 2B of the drawings, the suture anchor installation apparatus in accordance with the present invention is shown schematically. The installation apparatus includes a conventional hollow cannula 10, having a tubular portion 11 with an axial bore 12 and a radial flange 13 at its proximal end; a hollow cannulated drill guide 14 having a tubular portion 15 with an axial bore 16 and a laterally extending handle 17 at its proximal end; a hollow inner cannula 18 having a tubular portion 19 with an axial bore 20 and a laterally extending handle 21 at its proximal end; and a tubular anchor deployment tool 22 having an axial bore 23.

The exterior surface of the tubular portion 19 of the inner cannula 18 and the exterior surface of the tubular anchor deployment tool 22 are provided with longitudinally spaced markings 19A and 22A, respectively, along their length in equal graduations. The tubular portion 15 of the drill guide 14 is sized to be slidably received through the axial bore 12 of the conventional cannula 10 with its distal end extending a distance outwardly from the distal end of the cannula 10 (FIG. 1B). The axial bore 16 of the drill guide 14 is sized to receive the bone drill bit 24 of a conventional air drill 25. The bone drill bit 24 may optionally be provided with longitudinally spaced markings (not shown) along its length in equal graduations corresponding to the markings 19A and 22A on the tubular portion 19 of the inner cannula 18 and the exterior surf ace of the tubular anchor deployment tool 22.

As best seen in FIGS. 2A and 2B, tubular portion 19 of the inner cannula 18 is sized to be slidably received through the axial bore 16 of the drill guide 14 and is of sufficient length such that its proximal and distal ends extend outwardly from the proximal and distal ends of the drill guide. The inner cannula 18 may also be provided in sizes to be received in the axial bore 12 of the conventional cannula 10 for use in situations where the drill guide 14 is removed from the cannula 10. The tubular anchor deployment tool 22 is sized to be slidably received through the axial bore 20 of the inner cannula 18 and is of sufficient length such that its proximal and distal ends extend outwardly from the proximal and distal ends of the inner cannula (FIG. 2B). The side wall of the deployment tool may be provided with a short longitudinal slot 22B at its proximal end through which the upper free ends of sutures may be received.

Figure 4:
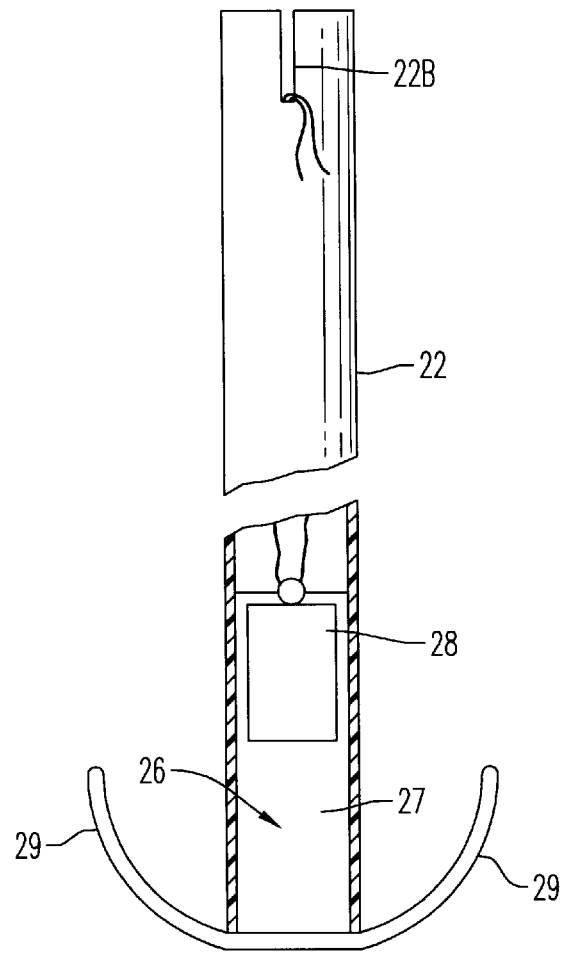
FIG. 4 is a side elevation showing the connection between the suture anchor and distal end of the anchor deployment tool.

Referring now to FIGS. 3 and 4 of the drawings, the soft tissue fastener or suture anchor 26 is shown somewhat schematically. The suture anchor 26 has a tubular shank 27 of predetermined length with an eyelet 28 at its proximal end and a plurality of circumferentially spaced wings 29 at its distal end which extend radially outward and rearwardly toward the proximal end of the anchor in the fashion of an inverted umbrella or grappling hook. The wings are resilient, such that they will be compressed and deflected radially inward when passed through a hole smaller in diameter than the wings in their outwardly extended state. The wings 29 are also of a predetermined length. In other words, if the total length of the anchor 26 is 1.5 cm., the longitudinal distance (height) of the wings 29 may be 0.5 cm.

Figure 5B:
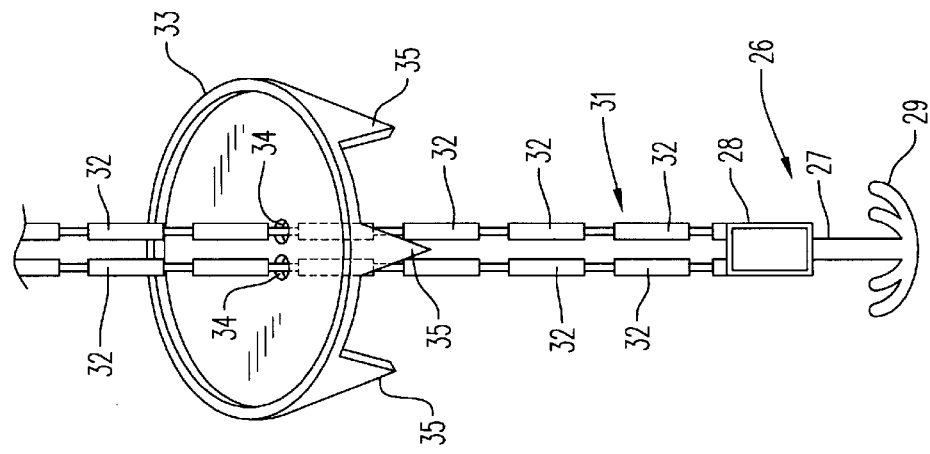
FIG. 5B is a perspective view showing the suture button with plastic strands having protuberances.
Figure 5A:
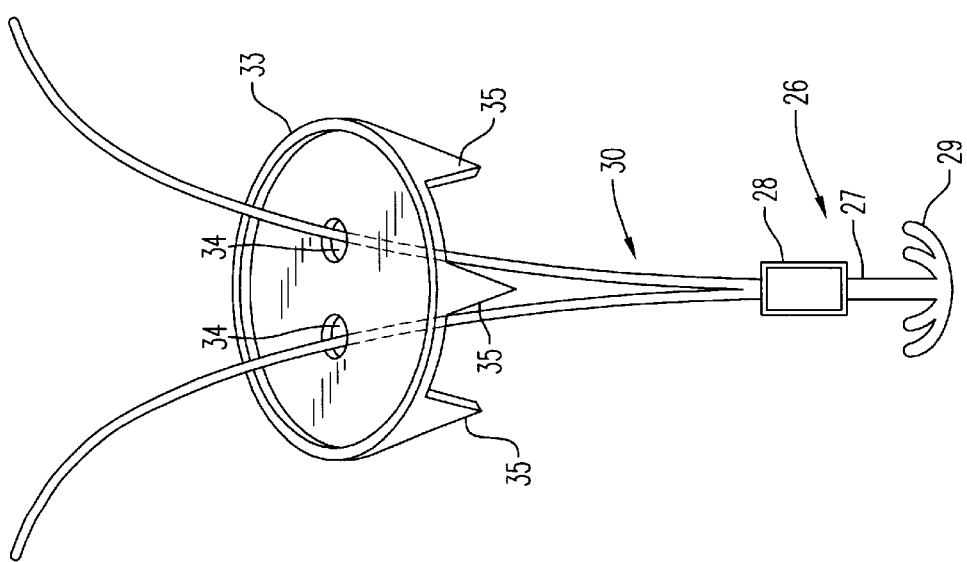
FIG. 5A is a perspective view showing the suture button with a conventional suture.

As shown in FIG. 5A, a conventional suture 30 may be secured to the eyelet 28 of the anchor 26 with two strands of the suture extending therefrom. Alternatively, as shown in FIG. 5B, a pair of special suture strands 31 may be secured to the eyelet 28. Each of the special suture strands 31 has a plurality of longitudinally spaced enlarged diameter portions or protuberances 32 along its length, similar to a plastic cable tie. The sutures 30 and 31 may be made of absorbable materials that absorb over a period of time, or they may be made of various non-absorbable, biocompatible materials.

A button 33 may be utilized with the anchor 26 and sutures 30 or 31 to attach the tendons of the rotator cuff to the bone. The button 33 is a disc-shaped member having two or more holes 34 through its flat surface through which the sutures 30 or 31 will pass. The protuberances 32 are slightly larger than the diameter of the holes 34 so as to snap through the holes upon sufficient force being applied. The button 33 may also have a plurality of circumferentially spaced prongs 35 depending from one side which can be pressed into the soft tissue of the rotator cuff.

Referring now to FIGS. 6A through 6E, to install the soft tissue fastener or anchor 26, the rotator cuff is held in the proper position by a conventional tissue grasper through an auxiliary portal. The conventional cannula 10 is inserted through the skin and the deltoid muscle onto the rotator cuff. The tubular portion 15 of the drill guide 14 is installed through the axial bore 12 of the cannula 10 with its distal end engaged on the rotator cuff.

Figures 6A, 6B:
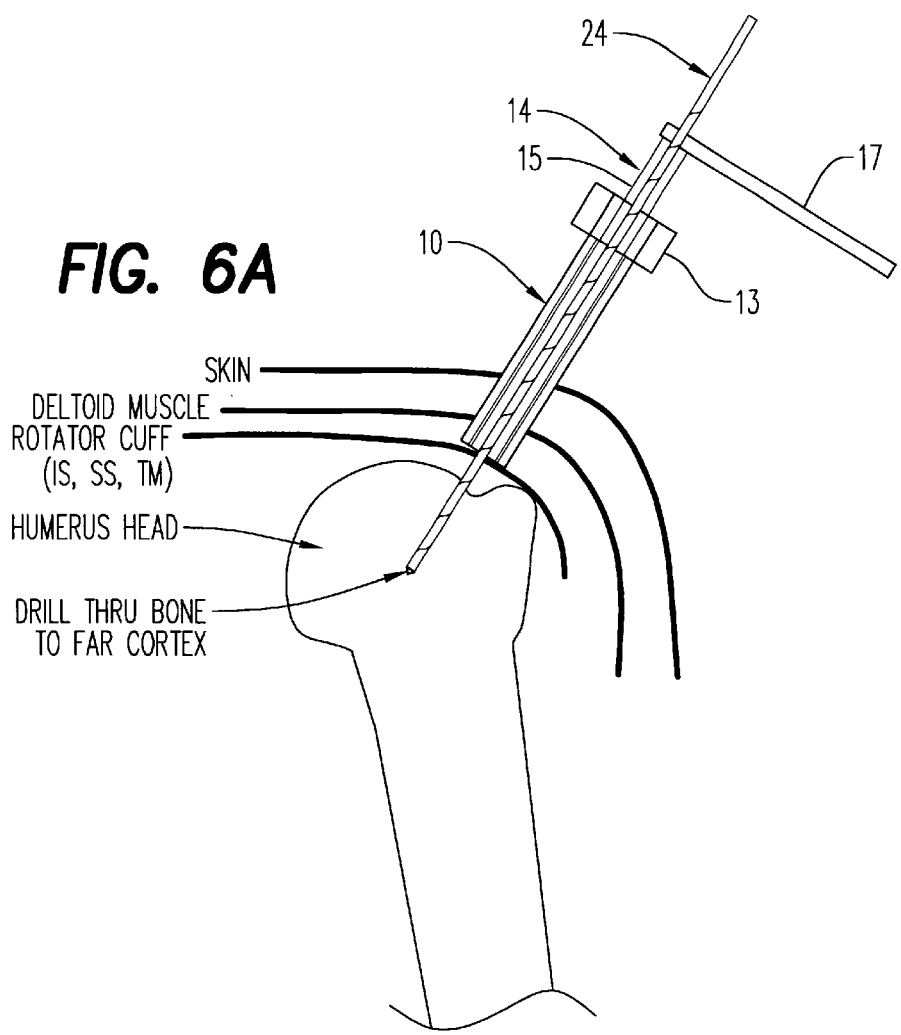
FIGS. 6A through 6E are schematic illustrations showing the various stages in installing the suture anchor.
Figure 6C:
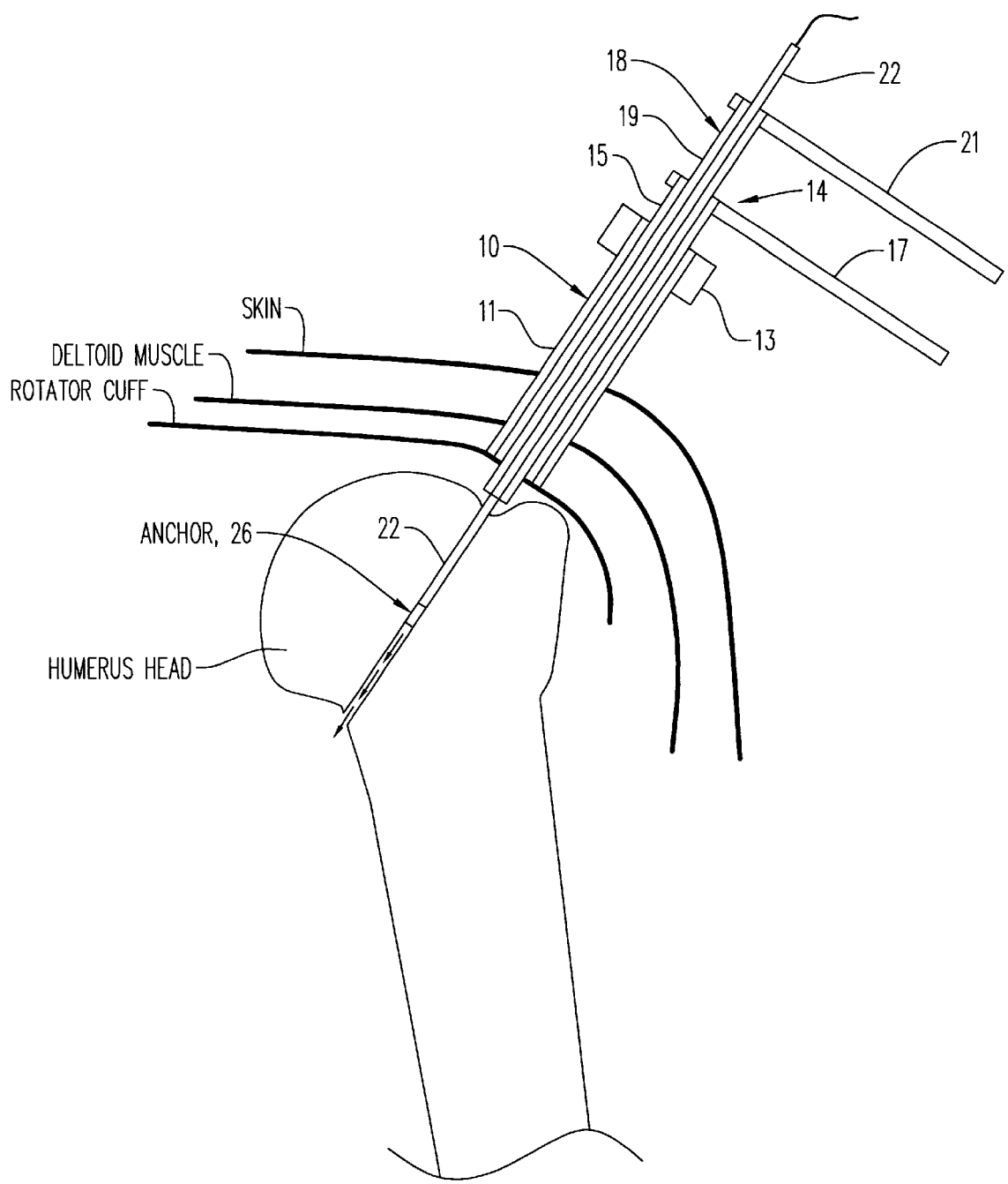
Figure 6D:
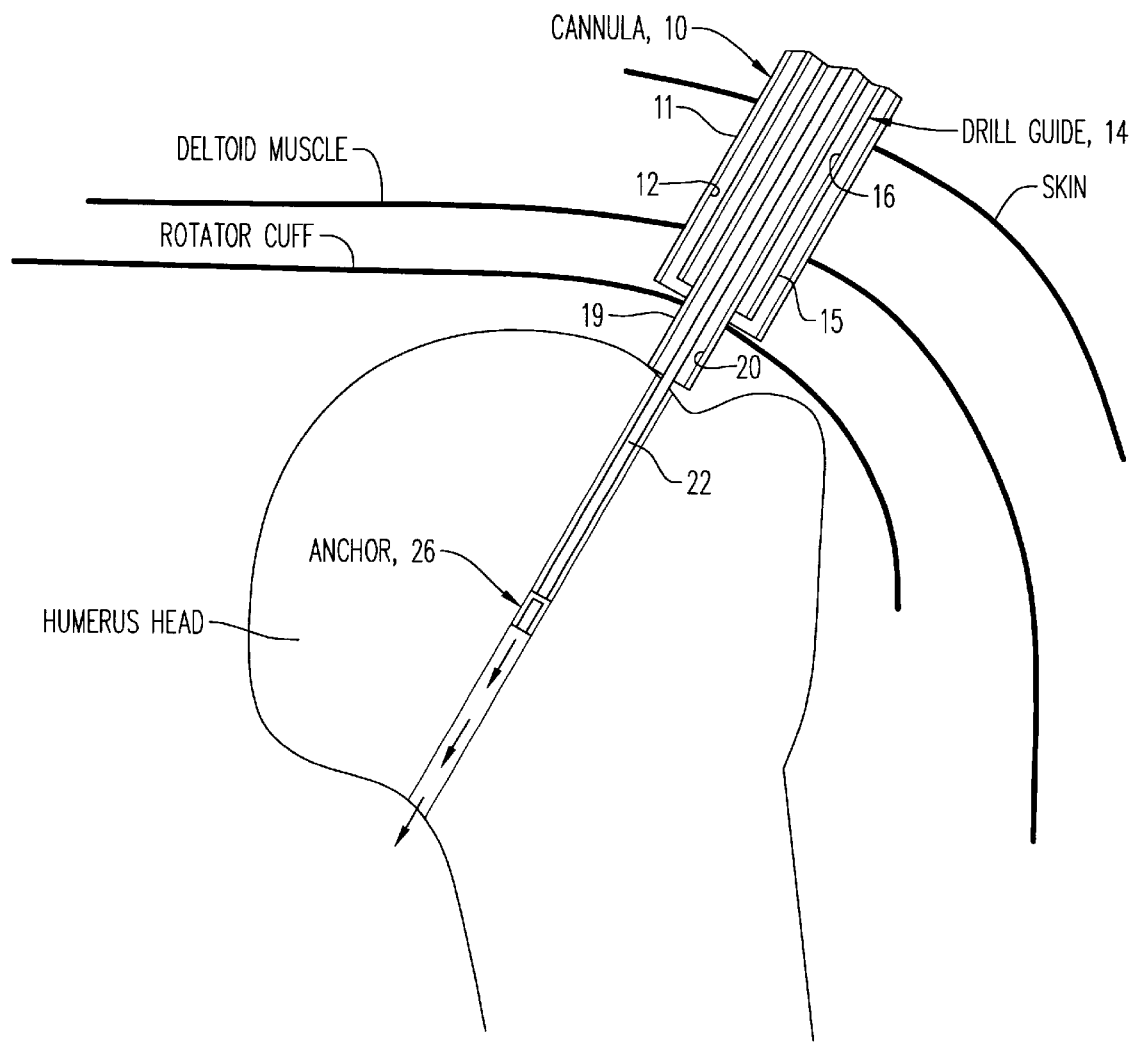

The bone drill bit 24 of the air drill 25 is inserted through the axial bore 16 of the drill guide 14 (FIG. 2B). A hole is then drilled through the tendon of the rotator cuff of the rotator cuff and completely through the humerus head (FIG. 6A). The drill bit is removed and the depth of the hole is determined using a depth gage. FIG. 6B is a top plan view showing three tendons of the rotator cuff having holes drilled through the tendon and humerus head. As shown in FIGS. 2B, 6C and 6D, the tubular portion 19 of the inner cannula 18 is installed through the axial bore 16 of the drill guide 14 and through the rotator cuff tendon with its distal end positioned adjacent to the distal end of the drill guide. Its position can be determined by the graduated markings on the exterior of its proximal end.

Alternatively, the tubular portion 19 of the inner cannula 18 may, be installed through the axial bore of the drill guide 14, through the rotator cuff tendon, and through the drilled hole with its distal end positioned at the far cortex of the humerus head (bottom of the hole). Its position can be determined by the graduated markings on the exterior of its proximal end. In some cases, the drill guide 14 may be removed from the conventional cannula 10 and the tubular portion 19 of the inner cannula 18 installed in the axial bore 12 of the conventional cannula 10.

The soft tissue fastener or anchor 26 is releasably connected to the distal end of the deployment tool 22. In one preferred connection embodiment, the tubular shank 27 and eyelet 28 of the anchor is slidably received inside the distal end of the deployment tool 22 with the strands of the suture 30 or 31 extending upwardly through the interior of the deployment tool 22. The upper free ends of the sutures 30 or 31 are pulled upwardly and placed through a slot 22B in the side wall of the deployment tool 22 to releasably retain the anchor 26 at the distal end to the deployment tool.

The assembled deployment tool 22 and anchor 26 is then inserted through the axial bore 20 of the inner cannula 18, causing the outwardly extended wings 29 of the anchor to become compressed and deflected radially inward by the interior of the inner cannula 18 as they pass therethrough.

Figure 6E:
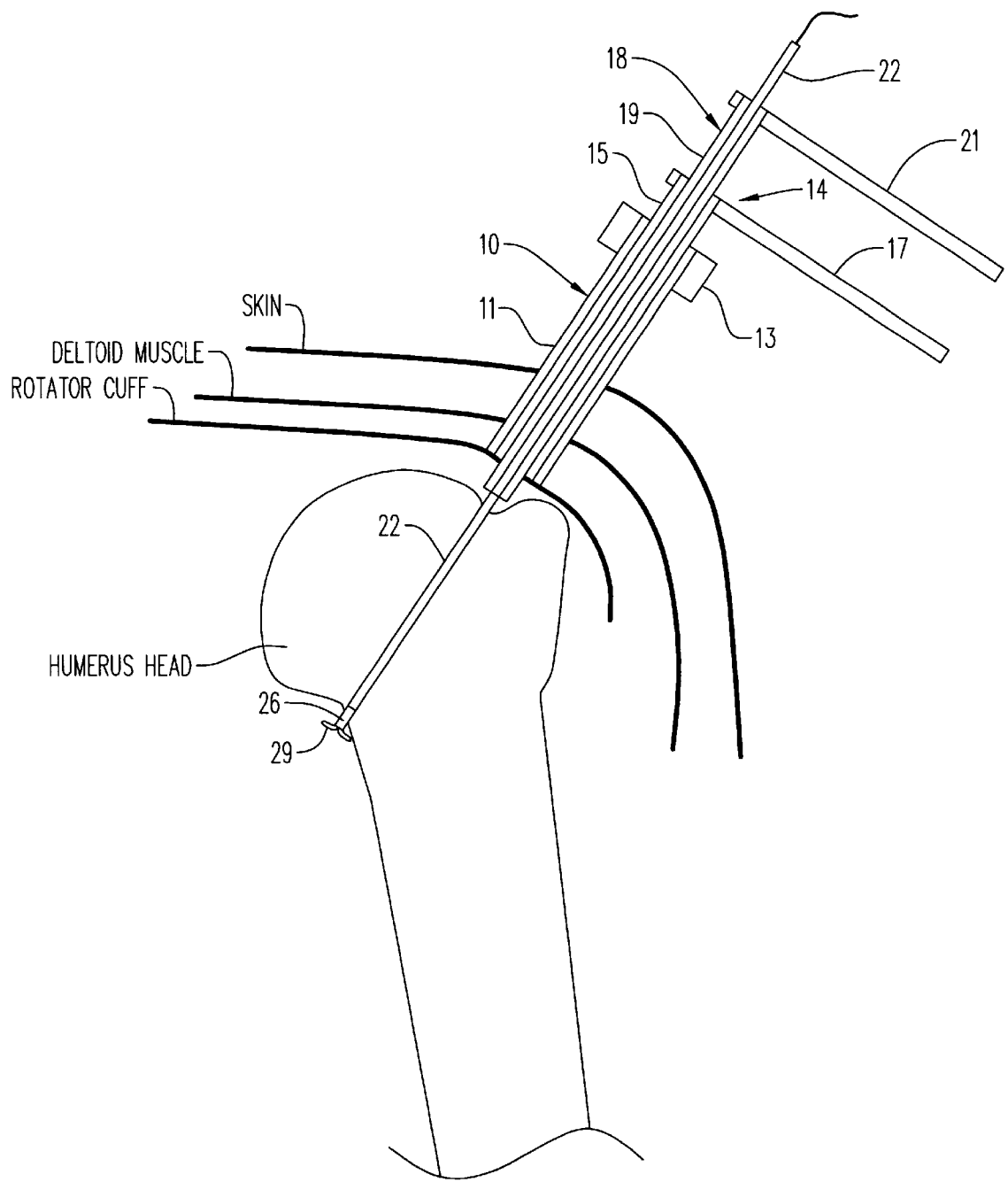

The assembled deployment tool 22 and anchor 26 is pushed downwardly through the inner cannula 18 until the inwardly biased wings 29 of the anchor 26 pass through the drilled hole and exit at the far end, at which point they spring outwardly to resume their original outwardly expanded state (FIG. 6E).

In some cases it may be desirable to place the inner cannula 18 through the drilled hole with its distal end positioned at the far cortex of the humerus head (bottom of the hole). In this situation, the assembled deployment tool 22 and anchor 26 is pushed downwardly until, the inwardly biased wings 29 of the anchor 26 clear the distal end of the inner cannula 18, at which point they spring outwardly to resume their original outwardly to resume their original outwardly expanded state (FIG. 6E). The position of the anchor and deployment tool can be determined by reading the graduated markings on the exterior at the proximal end of the deployment tool 22.

After the anchor wings 29 have been deployed, the upper free ends of the sutures are released from the slot 22B of the deployment tool 22, and the deployment tool 22, the inner cannula 18, and the drill guide 14 are removed. The strands of the sutures 30 or 31 which now extend through the drilled hole, the soft tissue of the rotator cuff, and the cannula 10 are pulled upwardly to firmly engage the outspread wings 29 of the anchor 26 against the exterior surface of the far cortex of the humerus head.

Referring again to FIGS. 5A and 5B, the proximal ends of the sutures 30 or 31 are passed through the holes 34 in the button 33, and the button is run down on the suture strands to engage the outer surface of the tendon of the rotator cuff. If the button 33 is provided with the prongs 35, they are pressed into the soft tissue of the cuff.

If the conventional sutures 30 are used, the sutures are tied or knotted in the conventional manner to secure the button 33. If the special sutures 31 having the longitudinally spaced protuberances 32 are used (FIG. 5B), the protuberances will snap through the holes 34 of the button 33 as it is run downwardly on the strands, similar to a cable tie. When the button 33 is properly engaged on the cuff, the excess length of the strands 31 are clipped off, leaving one of the enlarged protuberances 32 engaged on the outer flat surface of the button to secure it in place.

Thus, unlike conventional soft tissues anchors which are anchored in the cancellous bone mass beneath the near cortex of the bone, the present invention provides a suture anchor which is engaged on the exterior of the far cortex of the bone and completely bypasses the cancellous bone mass. The cortex of the bone is much less susceptible to osteopenia than the cancellous interior of the bone.

With the present invention, the sutures are passed through the tissue when the anchor is set, and thus the difficult procedural step and use of devices such as punches and suture relays to pass and tie the sutures through the torn tissue is eliminated.

The calibrated markings on the deployment system of the present invention allows for precise measurement of the far cortex and allows for precise measurement of the depth of insertion and engagement of the anchor device on the far cortex, such that structures beyond the cortex are not violated, and the button hold-down feature of the present invention eliminates the traditionally difficult arthroscopic tying techniques. The present method of repairing rotator cuff tears is "user friendly" and will allow more surgeons to employ this technique in their daily practice.

Referring now to FIGS. 7A through 7E, additional broader and preferred embodiments of the invention are there shown generally at numerals 40, 40a, 60 and 60a. In general, these embodiments disclose that the present invention is applicable to the reattachment of any torn or damaged body tissue or artificial material to any other type of human substrate tissue. For further example, a resorbable plate may be attached to bone substrate tissue, torn cartilage could be reattached to other cartilage substrate tissue and the like. Moreover, virtually any conventional well known tissue anchor may be utilized in conjunction with the other unique structural features of the herebelow described embodiments of the invention. Such tissue anchors are only attachable to or within bone tissue, but may also be attachable to cartilage, tendons, fascia, ligament and the like. This invention is also applicable not only to arthroscopic surgical techniques, but also open or conventional surgical techniques. The suture member itself, along with a separate lockingly engageable tissue retainer, may be formed of non-absorbable or reabsorbable material and may be either flexible, semi-flexible or substantially rigid as desired within the scope of this aspect of the invention.

Figure 7A:
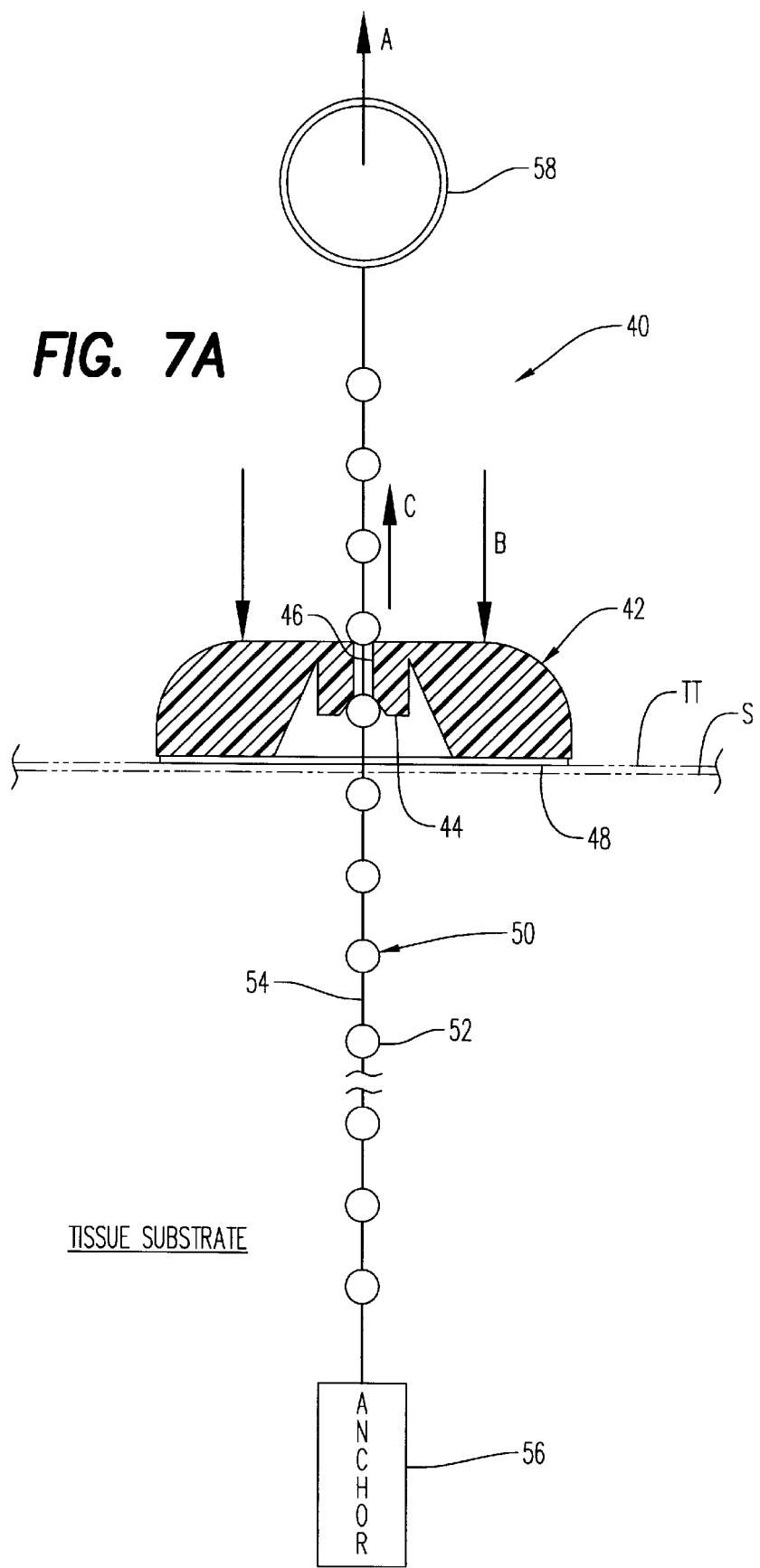
FIG. 7A is a side elevation partial section view of another and now preferred embodiment of the invention showing the structurally cooperative relationship between the elongated suture member, a tissue substrate anchor, and a separate tissue retainer.

In FIG. 7A, one embodiment of an elongated suture member is shown generally at numeral 50 formed as a semi-flexible member having a plurality of longitudinally spaced enlarged diameter portions or protuberances 52 along its length somewhat similar to a plastic cable tie as previously described. Each of the protuberances 52 are interconnected by integrally formed elongated strands or segments 54 of substantially smaller transverse size. A proximal end of the suture member 50 is attachable to a conventional well known tissue substrate anchor 56. A variety of such substrate anchors are available from sources such as Innovasive Devices, Inc., under their trademark CONTACK labral anchors.

A separate tissue retainer is shown generally at 42 and includes a central aperture 46 defined by flexible side walls 44 which are sized to be resiliently expanded apart as each of the successive protuberances 52 are forcibly pulled one at a time in the direction of arrow C through the resiliently expanded aperture 46. Once pulled upwardly through aperture 46 of the tissue retainer 42, the suture member 52 may not be reverse or retracted in the opposite direction with respect to the anchor 56.

A tissue gripping surface 48 is also preferred for increased retention of the torn tissue when the tissue retainer 42 is forcibly urged in the direction of arrow B against the torn tissue TT positioned over outer surface S of a tissue substrate. The tissue gripping surface 48 may be in the form of a textured surface of the molded plastic tissue retainer 42 or in the form of a separate layer having an abrasive surface. In any case, the tissue gripping surface 48 is generally intended to enhance prevention of relative movement between the torn tissue TT and the outer surface S of the tissue substrate into which the tissue anchor 56 has previously been secured. The degree of tensioning applied in the direction of arrows B against the torn tissue TT is determined by the surgical practitioner as the tissue retainer 42 is secured in position.

Referring to FIG. 7B, the same apparatus shown at 40 in FIG. 7A is repeated and shown at 40a. This embodiment 40a also includes a separate torn tissue gripping member 58 formed of thin flexible surgical steel having a substantially greater contact surface area than that of the tissue retainer 42. Thus, the tissue griping member 58 will flex to confirm into the position shown in phantom to be compliant against the shape of the torn tissue TT as it is placed against the outer surface S of the tissue substrate.

Figure 7C:
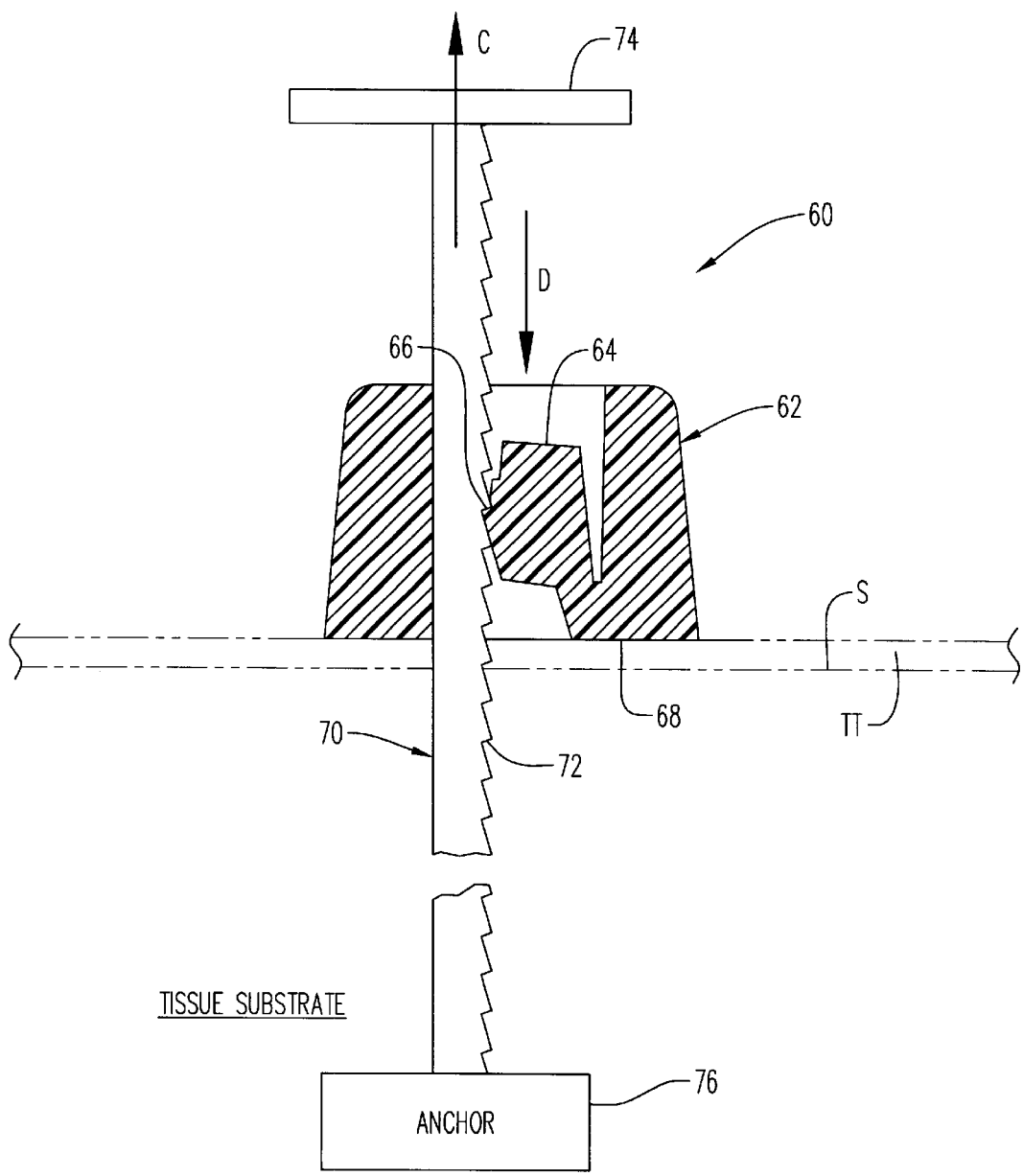
FIG. 7C is a side elevation partial section view of yet another now preferred embodiment of the invention.
Figure 7D:
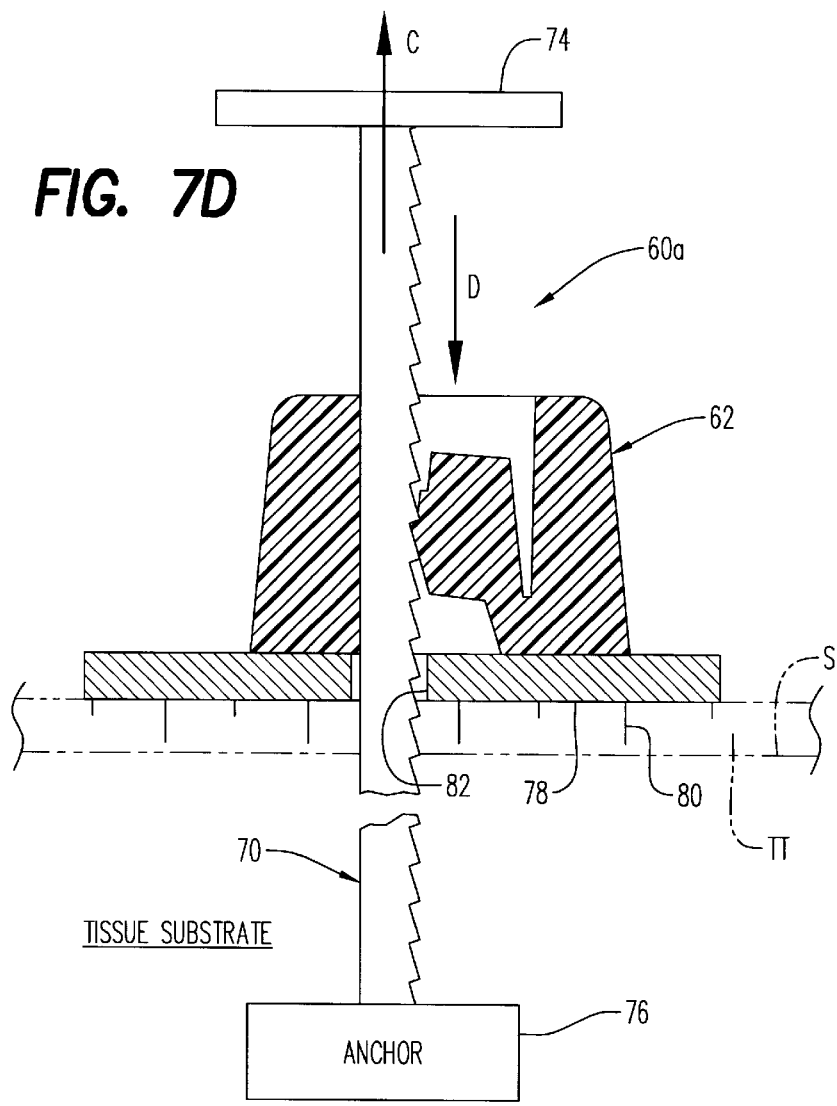
FIG. 7D is a side elevation partial cross section view of the invention shown in FIG. 7C with the addition of a separate tissue gripping member.
Figure 7E:
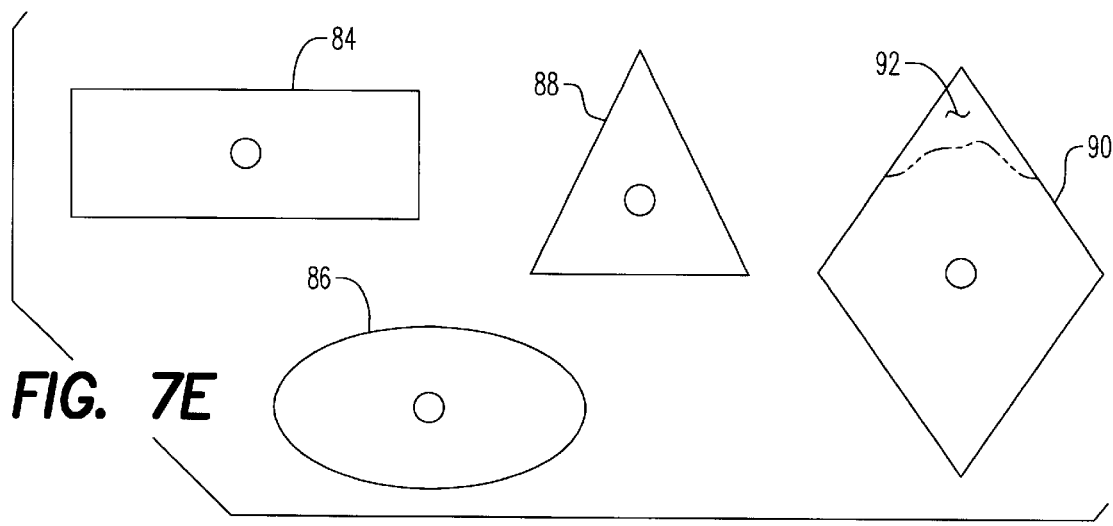
FIG. 7E shows a variety of alternate shape embodiment of the tissue gripping member or plate of FIG. 7B.

A virtually limitless variety of plan view shapes of the torn tissue gripping member 58 are shown in FIG. 7E at 84, 86, 88, and 90. Each of these torn tissue gripping members include a central aperture sized for freely receiving the protuberances 52 of the suture member 50 as previously described. Each of the torn tissue gripping members may be modified as shown by example with respect to 90 in FIG. 7E wherein a portion 92 is removed at the time of surgical placement atop the torn tissue.

Referring now to FIGS. 7C and 7D, two further embodiments of the invention are shown generally at numeral 60 and 60a, respectively. In FIG. 7C, a tissue retainer is shown generally at numeral 62 formed of molded inert plastic material. A separate suture member 70 having spaced notches or teeth 72 extending along side margin thereof. A proximal end of the suture member 70 is connectable to a tissue substrate anchor 76, again of a conventional well known nature as previously described. This suture member is flexible in one plane and substantially rigid in the plane of the paper as shown.

The tissue retainer 62 includes a flexible locking portion 64 having an engaging tooth 66 which pivotally and resiliently moves to effect locking engagement with a selected one of the notches 72 so that, when an optional disconnectable handle 74 of the distal or exposed end of the suture member 70 is pulled in the direction of arrow C against resistive force applied to the retaining member 62 in the direction of arrow D, relative non-reversible tightening movement increasing the pressure of the gripping surface 68 against the torn tissue TT placed atop surface A of the tissue substrate is lockingly maintained. Thus, the surgical practitioner may vary the retaining force applied against the torn tissue TT in this manner as desired.

The embodiment 60a in FIG. 7D disclose the same apparatus structure of FIG. 7C with the addition of a separate generally rigid torn tissue gripping member 78 which includes a central hole 82 through which the suture member 70 will freely pass. Prongs 80, downwardly extending into the torn tissue TT, in combination with the torn tissue gripping surface area provided by the separate gripping member 78 more fully insure maximum immobilization and securement of the torn tissue TT atop the outer surfaces of the tissue substrate.

Figure 8:
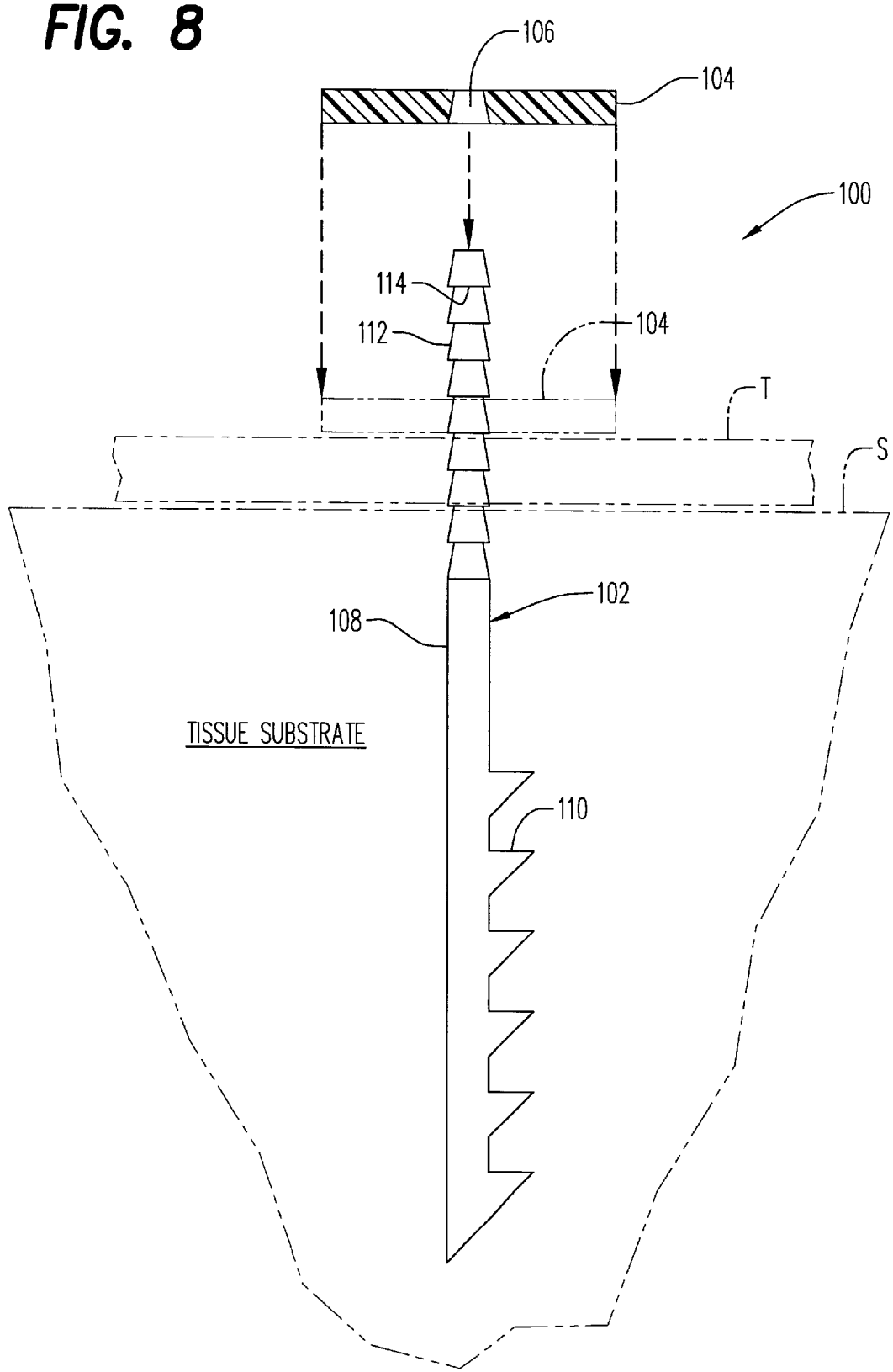
FIG. 8 is a side elevation partial section view of still another preferred embodiment of the invention showing the structurally cooperative relationship between the elongated suture member, a tissue layer and a separate tissue substrate to which the tissue layer is attached.
Figure 9:
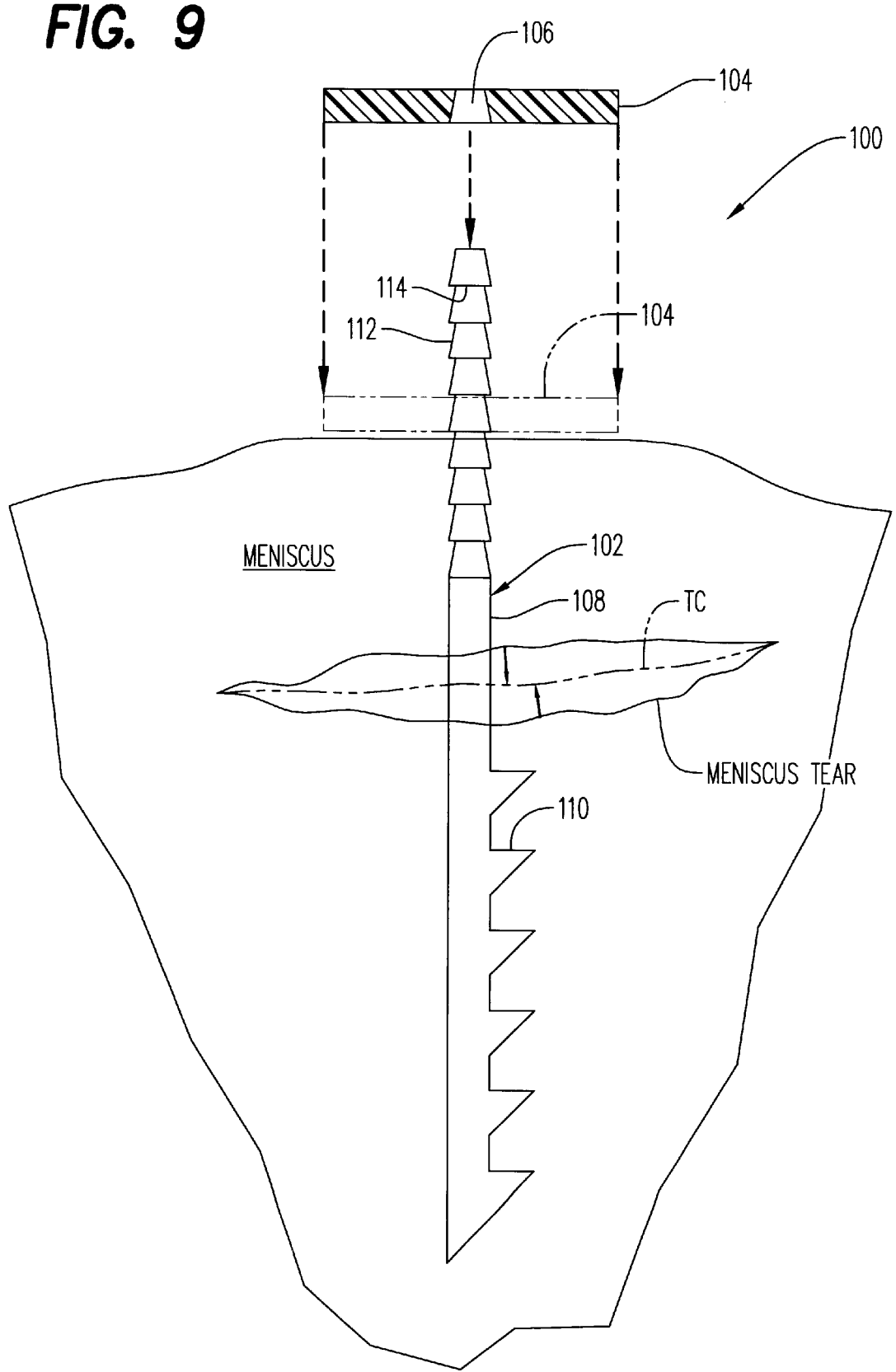
FIG. 9 is an alternate use of the embodiment of the invention shown in FIG. 8.

Referring now to FIGS. 8 and 9, yet another preferred embodiment of the invention is shown generally at numeral 100 and includes an elongated suture member shown generally at 102 and a tissue retainer 104. The suture member is formed as a unit having a tissue anchor portion 110 extending from one end thereof which includes tissue engaging teeth suitably shaped to be able to forcibly pierce into the tissue substrate and then to prevent any substantial withdrawal of the anchor portion from the tissue substrate. The opposite end portion 112 of the suture member 102 includes spaced engaging members 114 which are shaped as either trapezoids or truncated conical segments, depending upon whether a generally flat or a circular cross section to this portion 112 of the invention is desired.

The tissue retainer 104 includes a central locking aperture 106 and, by its preferred flat disc-shaped configuration, defines a lower tissue gripping surface thereof. The locking aperture 106, when forcibly urged in the direction shown by the arrows over each successive engaging member 114, is irreversibly prevented from movement in the opposite direction of any substantial amount.

In FIG. 8, this tissue anchoring device 112 is shown secured within a tissue substrate having an exposed surface S against which a tissue layer T has been positioned after being pierced through and slid over the exposed anchor portion 112. Thereupon, the tissue retainer 104 is forcibly urged over each successive engaging member 114 to its final position shown in phantom whereupon a clamping force is exerted between the tissue substrate and the tissue layer T against the outer surface S of the tissue substrate.

In FIG. 9, the same tissue anchoring device 100 is shown in position relative to a meniscus substrate having an internal meniscus tear therewithin. By forcibly deploying the anchor portion 110 through the meniscus tear so that a central smooth portion 108 of the suture member 102 spans the tear, forcibly urging the tissue retainer 104 over the engaging members 114 one at a time to effect a desired closing tension across the meniscus tear, closure thereof is effected along phantom line TC. This closure is maintained by the tension or closure force exerted by the tissue retainer across the now closed meniscus tear.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A surgical suture member for arthroscopic reattachment of torn tissue to a tissue substrate, consisting of:

an elongated suture member securable at one end thereof to a tissue substrate anchor and having a free end extending therefrom and further having a plurality of longitudinally spaced protuberances or notches along a portion of its length;

a tissue retainer having a locking aperture or cavity extending therethrough adapted for locking engagement with one said protuberance or notch;

said free end of said suture member being insertable through said locking aperture or cavity and said protuberances or notches lockingly engaging with said locking aperture or cavity as said tissue retainer is run down on said suture member to retainingly engage against an outer surface of the torn tissue;

a torn tissue gripping member having a hole formed centrally therethrough sized to freely receive said suture member and defining a gripping surface;

said gripping member being formed of a semi-flexible generally concaved plate of substantially greater surface area than that of said retaining member;

said gripping member, when positioned between said tissue retainer and the torn tissue and said free end of said suture member is placed through said hole and tension applied thereto, enhanced gripping and retaining engagement of the torn tissue against the tissue substrate is maintained.

* * * * *